United States Patent [19]

Dysart et al.

[11] Patent Number: 4,578,073
[45] Date of Patent: Mar. 25, 1986

[54] COMPOSITE WASTE-CONTAINMENT GARMENT HAVING DISPOSABLE ELASTICIZED INSERT

[75] Inventors: John K. Dysart; Frederick M. Joffe, both of Cincinnati, Ohio

[73] Assignee: The Procter & Gamble Company, Cincinnati, Ohio

[21] Appl. No.: 508,444

[22] Filed: Jun. 27, 1983

[51] Int. Cl.$^4$ ............................................. A61F 13/16
[52] U.S. Cl. ................................. 604/397; 604/385 A
[58] Field of Search ............... 604/385, 389, 390, 393, 604/394, 398, 399, 397

[56] References Cited

U.S. PATENT DOCUMENTS

| | | | |
|---|---|---|---|
| 4,182,333 | 1/1980 | Schaar | 604/390 |
| 4,205,679 | 6/1980 | Repke et al. | 604/394 X |
| 4,388,075 | 6/1983 | Mesek et al. | 604/385 |

Primary Examiner—C. Fred Rosenbaum
Assistant Examiner—Christa K. Scott
Attorney, Agent, or Firm—Thomas J. Slone; Fredrick H. Braun; Richard C. Witte

[57] ABSTRACT

A composite waste-containment garment comprising a disposable, elasticized waste-containment insert secured by means integral with the insert inside a non-elasticized over-garment such as a conventional reuseable diaper, or a disposable diaper, or overpants, or the combination of a non-elasticized reuseable diaper covered with an outer-garment such as overpants having elasticized leg cuffs. The insert comprises an absorbent core and a liquid impervious backsheet. Preferably, it also includes a liquid pervious, hydrophobic topsheet. The insert has a width less than one-half the midsection girths of intended users and, preferably, the absorbent core has front and back waist portions which have widths of from about fifteen to about thirty-five percent of the midsection girths of intended users, or about one-quarter the midsection girth of nominally sized intended wearer. The insert is so elasticized along its longitudinal side edges that, when properly secured inside a suitable over-garment, and the over-garment is properly applied to a wearer as with safety pins, the elasticized side edges of the insert are sufficiently tensioned to form liquid seals or leg cuffs along upper thigh regions of the wearer: particularly, along the inner spans of the upper thigh regions of the wearer. The insert may include outwardly facing adhesive areas on its corners to enable its securement to inwardly facing surface regions of the over-garment; and the insert may futher include captive peelable covers for the adhesive areas.

11 Claims, 8 Drawing Figures

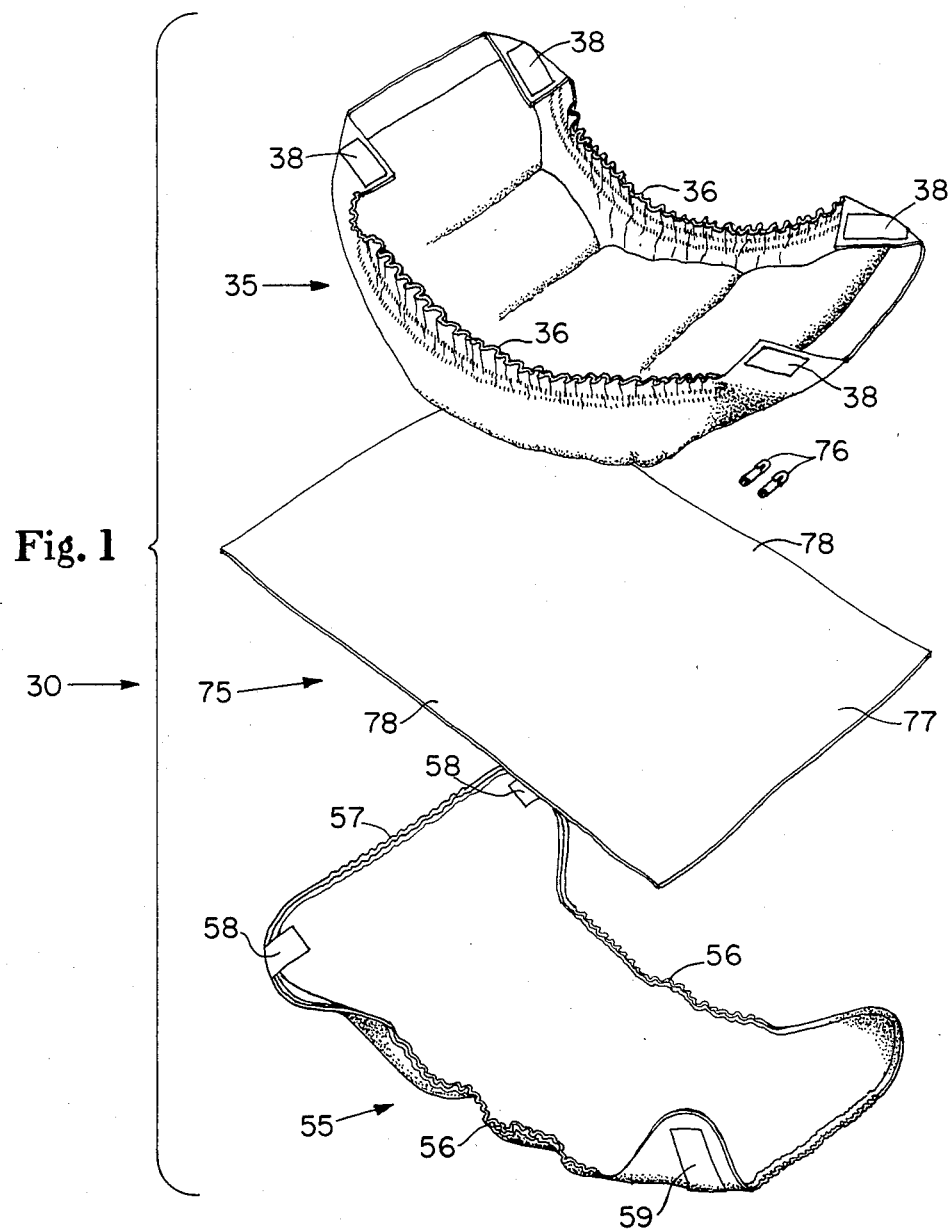

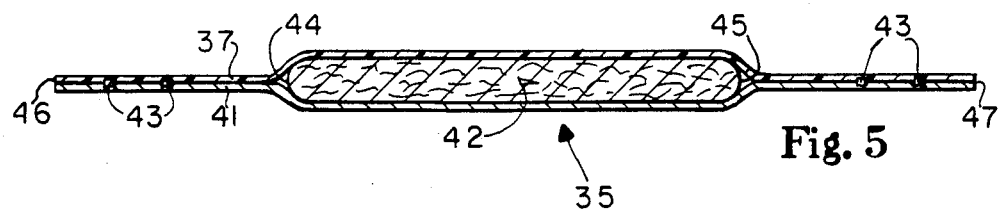
Fig. 5
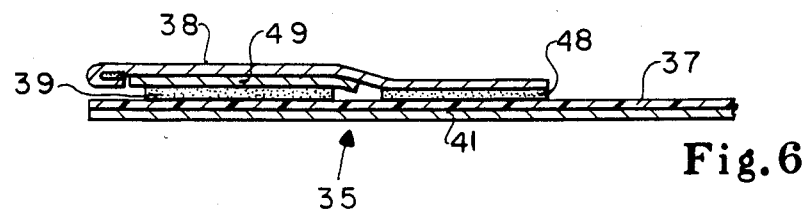
Fig. 6
Fig. 7
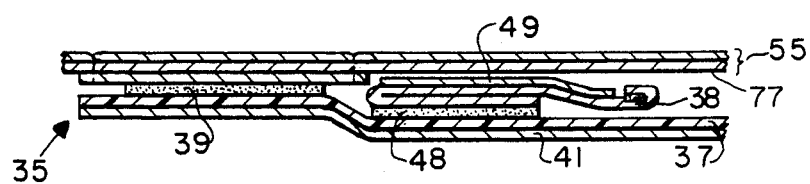

COMPOSITE WASTE-CONTAINMENT GARMENT HAVING DISPOSABLE ELASTICIZED INSERT

DESCRIPTION

1. Technical Field

This invention pertains to absorbent pads for external application and supports therefor: for example, disposable diapers but more particularly to an elasticized disposable insert in combination with an over-garment such as a reuseable diaper, a disposable diaper, or overpants, and the like. The insert of the present invention may be secured inside such an over-garment with securement means such as adhesive areas on the insert which are disposed and configured to so secure the insert within a complementary over-garment that the leg cuffs of the insert are sufficiently stretched upon applying the over-garment to a wearer that the leg cuffs of the insert are sealingly engaged with skin areas of the wearer.

2. Background Art

Non-elasticized diaper inserts or liners are shown in a number of U.S. patents. Representative U.S. patents include U.S. Pat. No. 2,141,105 which issued Dec. 20, 1938, to J. A. Eller et al and shows an absorbent pad secured inside a holder with bands or tapes which may be elastic: U.S. Pat. No. 2,292,030 which issued Aug. 4, 1942 to M. Kraft, U.S. Pat. No. 2,577,398 which issued Dec. 4, 1951 to V. Blake, and U.S. Pat. No. 2,606,558 which issued Aug. 12, 1952 to H. O. Kennette which show liners secured with snap fasteners inside side-closing overpants; U.S. Pat. No. 4,022,210 which issued May 10, 1977 to Jacob A. Glassman and shows a liner secured to a diaper with spots of pressure sensitive adhesive. Additionally, U.S. Pat. No. 2,733,715 which issued Feb. 7, 1956 to Y. L. Folk discloses Composite Training Pants and Diaper having unitized elasticized leg cuffs: leg cuffs wherein the longitudinal side edges of the training pants are joined to the longitudinal side edges of the diaper and jointly elasticized by elastic bands. Also, U.S. Pat. No. 3,860,003 which issued Jan. 14, 1975 to Kenneth Barclay Buell discloses an integral disposable diaper having contractable side portions (i.e., elasticized leg cuffs); and U.S. Pat. No. 4,211,226 which issued July 8, 1980 to Charles H. Schaar discloses a disposable diaper with a captive peelable flap covered tape fastener. While these patents disclose liner, diaper and outer-garment configurations and combinations which have solved some of the problems associated with providing waste-containment garments—particularly those comprising liners or inserts—they have not solved the problems to the same extent or degree as enabled by the present invention: i.e., by providing disposable, elasticized waste-containment inserts for use in a variety of over-garments so that the over-garments are protected against soilage by elasticized-leg-cuffs of the inserts. Thus, light capacity inserts embodying the present invention can be used with conventional diapers, disposable diapers, and other suitable over-garments to reduce the frequency of changing the over-garments. That is, for example, the present invention obviates the need to change heavy duty conventional or disposable diapers or the like after light soiling such as by a relatively low volume urine discharge.

DISCLOSURE OF THE INVENTION

In accordance with one aspect of the present invention, a waste-containment garment is provided which comprises an elasticized leg-cuff insert, an over-garment, and means for securing the insert in the over-garment prior to applying the over-garment to a wearer that, upon applying the over-garment to a wearer, the leg-cuffs of the insert are sufficiently stretched to sealingly engage them with skin surfaces of the wearer: preferably inwardly facing upper thigh areas of the wearer but which may include outwardly facing upper thigh areas and/or abdominal areas and/or hip areas of the wearer. Preferably, the insert comprises an absorbent core, a liquid impervious backsheet, and elasticized longitudinally extending leg cuffs disposed adjacent longitudinally extending side edges of the core. Such an insert may be rectangular or hourglass shape; and may include adhesive means disposed on its outwardly facing corners to enable attaching it to the inwardly facing surface of an over-garment. Additionally, such adhesive means may be provided with captive peelable cover means for protecting the adhesive means prior to use, and for obviating severable members which might otherwise present inherent safety problems. The composite garment may also comprise an outer-garment such as overpants having elasticized leg cuffs so that the composite garment comprises two sets of independently elasticized leg cuffs which are both activated upon applying the composite garment to a wearer albeit the two sets of cuffs are independently elasticized.

BRIEF DESCRIPTION OF THE DRAWINGS

While the specification concludes with claims particularly pointing out and distinctly claiming the subject matter regarded as forming the present invention, it is believed the invention will be better understood from the following descriptions taken in conjunction with the accompanying drawings in which:

FIG. 1 is an exploded perspective view of an exemplary, 3-element waste-containment garment embodiment of the present invention which comprises a disposable elasticized leg-cuff insert, an over-garment which as shown is a conventional cloth diaper, and an outer-garment which as shown above is side-closing overpants having elasticized leg cuffs.

FIG. 5 is a fragmentary sectional view taken along line 5—5 of FIG. 2.

FIG. 6 is a fragmentary sectional view taken along line 6—6 of FIG. 2.

FIG. 7 is a fragmentary sectional view of the adhesive fastener area shown in FIG. 6 after the cover for the adhesive has been peeled back and the adhesive area secured to the inwardly facing surface of an over-garment such as shown in FIG. 3.

DETAILED DESCRIPTION OF THE INVENTION

Figure 3:
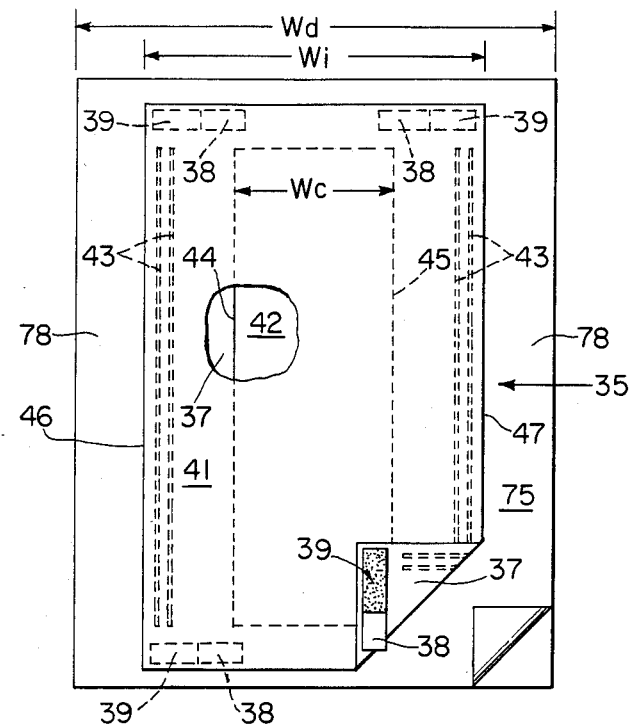
FIG. 3 is a plan view of the waste-containment insert shown in FIG. 2 in juxtaposed relation with a rectangular-shape conventional cloth diaper, and with one corner of the insert turned back.

An exemplary, 3-element, composite waste-containment garment 30 is shown in FIG. 1 to include a waste-containment insert 35 having elasticized leg cuffs 36, an outer-garment 55 having elasticized leg cuffs 56, a non-elasticized over-garment 75 such as a conventional cloth diaper disposed intermediate insert 35 and outer-garment 55 and having a rectangular shape, and means such as safety pins 76 for securing the non-elasticized over-garment 75 about a wearer.

Briefly, the insert 35 is secured to the inwardly facing surface 77 of the non-elasticized member 75 by means integral with the insert after the insert has been sufficiently stretched to substantially reduce its elastic induced contraction. Then the non-elasticized member (having an insert secured therein) is applied to and secured about a wearer so that the elastic leg cuffs 36 of the insert 35 are sealingly sengaged or juxtaposed skin areas of the wearer by stretching induced tension in the elasticized leg cuffs. The outer-garment 55 is then applied to entirely cover the combination of insert 35 and the non-elasticized over-garment 75, and side closures of the outer-garment 55 are secured. Finally, the elements of the composite garment are dressed (i.e., manually positioned) so that the longitudinally extending side edge regions 78 of the non-elasticized over-garment 75 are disposed intermediate the leg cuffs 36 and the leg cuffs 56, and so that all (i.e., 36, 56 and 78) are in contacting relation with the wearer's skin. Generally only the insert of such a composite garment needs to be changed upon light soiling as by low volume liquid or solid voiding by the wearer inasmuch as the elastic leg cuffs 36 of the insert 35 generally protect the other members 55 and 75 of the garment 30 from soiling. However, both the insert 35 and the outer-garment 55 may have to be changed following heavier voiding. In this event, the leg cuffs 56 of the outer-garment 55 as well as its general liquid impervious construction protect the wearer's other clothing from being soiled.

Figure 2:
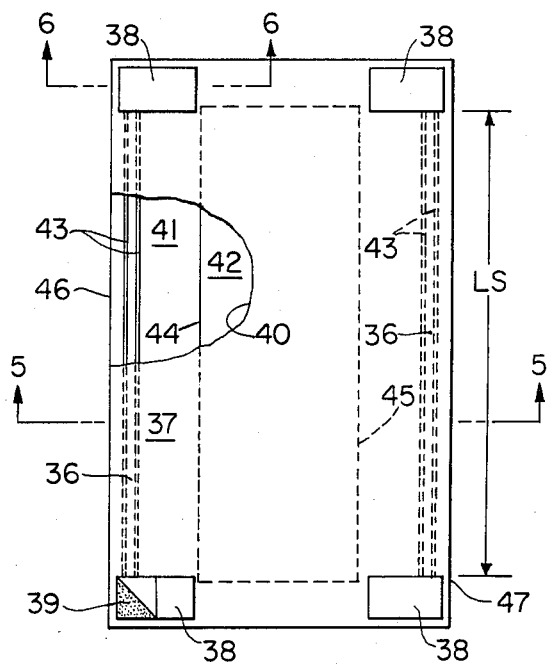
FIG. 2 is a plan view of the waste-containment insert of the composite waste-containment garment shown in FIG. 1 which view is taken looking at the outwardly facing surface of the backsheet of the insert with the insert in a non-contracted state: i.e., flat out rather than being contracted by the strands of elastic disposed in its leg cuff areas.

Referring now to FIG. 2, an exemplary waste-containment insert 35 is shown to comprise elasticized leg cuffs 36, and a backsheet 37 having a captive peelable cover member 38 covering an adhesive area 39 disposed on each of its four corners, one cover 38 being partially peeled back in FIG. 2 to reveal one of the four adhesive areas 39. Additionally, as shown in FIG. 2, a portion of backsheet 37 is torn away forming torn edge 40 which reveals the structure of insert 40 disposed behind backsheet 37 in FIG. 2. Such structure includes topsheet 41, absorbent core 42, and elastic strands 43. The side edges of the core 42 are designated 44 and 45; and the side edges of the insert 35 are designated 46 and 47.

An exemplary insert 35 was constructed in which the backsheet 37 is a matte-finish polyethylene film having a nominal thickness of about one mil (about 0.0254 mm), and overall length and width of about fifteen inches by about eight inches, respectively (about 38.1 by 20.3 cm, respectively); the topsheet 41 is a non-woven polypropylene also having a nominal thickness of about one mil, and length and width about equal to the corresponding dimensions of the backsheet; an air laid fibrous core having a nominal weight of about 30.7 grams, a nominal caliper of about 7.1 mm, and length and width of about thirteen by four inches, respectively (about 33 by 10.2 cm, respectively); strands 43 of elastic having nominal unstretched thickness and width of about 0.2 and 2.4 mm, respectively and which had been stretched about one-hundred-twenty-five percent (125%) prior to being adhesively secured to the backsheet, and prior to adhesively securing the topsheet of the backsheet whereby the longitudinal side edges of the insert (i.e., the elasticized leg cuffs 36) have nominal extensions (i.e., their available stretch as a percent of their elastically contracted length) of about one-hundred-twenty-five percent. Additionally, the core was enveloped with a low basis weight tissue paper not shown to provide structural integrity.

As further shown in FIG. 2, the elastic strands 43 extend longitudinally between adhesive areas which are covered with peelable covers 38, and the strands are disposed adjacent the superimposed longitudinal side edges of the topsheet and backsheet. In the exemplary insert, the inboard edge of the elastic strand 43 disposed closest to the absorbent core 42 is spaced therefrom about one-and-seven eighths inches (about 4.76 cm) whereby the elasticized leg cuffs—being relatively wide—can be contracted and stretched without having to induce crumpling or longitudinal compression of the core. Thus, stretching induced tension is available for sealingly engaging the leg cuffs 36 with skin areas of a wearer rather than being vitiated by trying to longitudinally compress the core. FIG. 2 also shows that portions of the adhesive areas having covers 38 are disposed in longitudinal alignment with the elastic strands 43, and that the adhesive areas having covers 38 are longitudinally spaced a distance LS apart. In the exemplary insert LS is about thirteen inches (about 33 cm).

In FIG. 3, insert 35 is shown in superposed relation with a 2-ply cloth diaper 75: i.e., an exemplary non-elasticized over-garment 75, FIG. 1. As shown in FIG. 3, insert 35 is disposed with its topsheet 41 facing upwardly so that its backsheet 37 is juxtaposed diaper 75. One corner of insert 35 is turned back to show an adhesive area 39 which has had its cover 38, FIG. 2, peeled back. Thus, the uncovered adhesive areas 39 disposed on each of the 4-corners of insert 35 constitute means integral with the insert for it to be adhesively secured to inwardly facing surface areas of diaper 75 which are longitudinally as well as transversely spaced the same distances as the adhesive areas are spaced on insert 35 when insert 35 is stretched to its full uncontracted length. Additionally, as shown in FIG. 3, covers 38 are captive to obviate severable members which might otherwise present safety problems. The covers 38 are discussed more fully hereinafter in conjunction with describing FIGS. 6 and 7.

As also shown in FIG. 3, the width of the core 42 is designated $W_c$; the width of the insert is designated $W_i$; and the width of diaper 75 is designated $W_d$. Preferably, $W_c$ is from about fifteen (15) to about thirty-five (35) percent of the midsection girth of an intended wearer albeit it may nominally be about one-quarter of the midsection girth of an average size wearer; $W_i$ is preferably somewhat less than one-half the midsection girth of an intended wearer whereby pinning or otherwise directly securing the insert about a wearer by overlapping corners thereof is obviated; and $W_d$ is preferably somewhat greater than one-half the midsection girth of an intended wearer to facilitate securing the diaper (with an insert 35 secured therein) about a wearer as by pinning the right front corner to the right back corner, and the left front corner to the left back corner with safety pins 76, FIG. 1; i.e., the common contemporary manner of pinning a reuseable cloth diaper on an infant.

Referring back to FIG. 1, outer-garment 55 which is alternatively referred to as overpants 55 is shown to have elasticized leg cuffs 56; elasticized back-waistband 57; and hook and loop type side-closure fastener means such as Velcro (registered trademark of Velcro USA Inc.) which comprise swatches 58 of hook-type fastener material which have been sewn to the inside of the back corners of the overpants and swatches 59 of loop-type fastener material which have been sewn to each outside front corner of the overpants but only one of which swatch 59 is visible in FIG. 1. Such overpants preferably have a liquid impervious construction which may comprise a liquid impervious layer of material disposed outside of a soft fabric topsheet (i.e., innermost ply), and which may have a soft fabric backsheet (i.e., outmost ply which may be decoratively adorned with lace and the like, not shown. An exemplary quality overpants comprising Velcro side-closure means, elasticized leg cuffs, and an elasticized back-waistband is marketed in a variety of sizes by Nishiki K. K. under the Brand name of Semi Cot Proof in Japan. This has a generally liquid impervious construction although its leg cuffs are believed to a breathable, porous construction.

Figure 4:
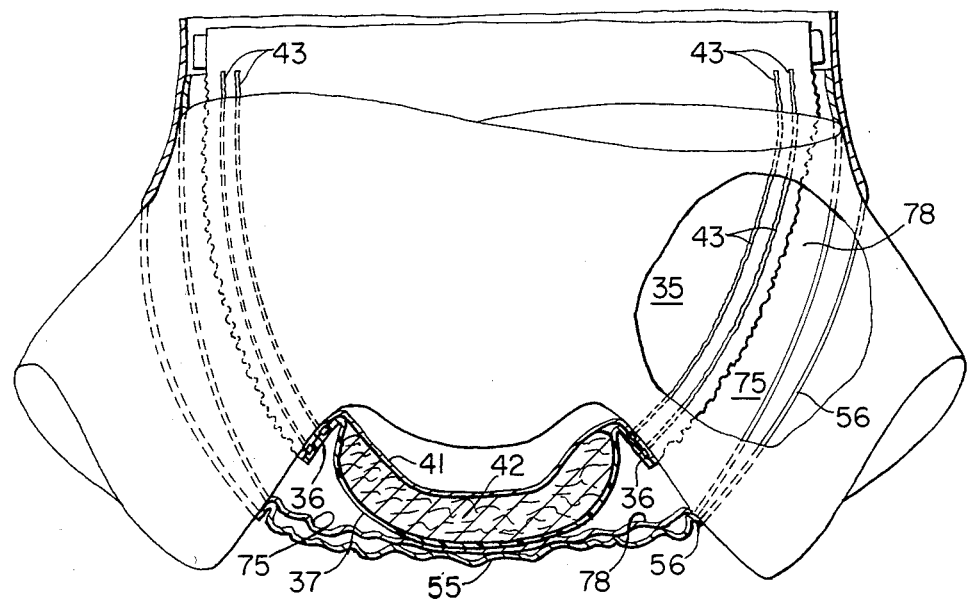
FIG. 4 is a fragmentary, side-to-side vertical sectional view of the composite waste-containment garment of FIG. 1 secured about a fragmentary portion of a wearer; i.e., the lower torso and upper thighs of an infant.

FIG. 4 is fragmentary, side-to-side vertical sectional view of the composite waste-containment garment 30, FIG. 1, which is secured about a fragmentary portion of a wearer. The garment was applied by first securing an insert 35 to a diaper 75 as described above in conjunction with describing FIG. 3; then, that subassembly was pinned on the wearer as also described above; and then the outer-garment 55 was secured in place over the diaper upon fastening its side closure fasteners. The leg cuffs 36 and 56, of the insert 35 and outer-garment 55, respectively, and the longitudinal side edge regions 78 of diaper 75 were then manually positioned so that all were in skin contracting relation with the wearer, and so that each side edge region 78 was disposed intermediate a leg cuff 36 of the insert and a leg cuff 56 of the outer-garment/overpants 55.

FIG. 5 is a transverse sectional view taken along line 5—5 through the waste-containment insert 35, FIG. 2. As shown in FIG. 5, the backsheet 37 and topsheet 41 of insert 35 are joined together along the longitudinal side edges 44 and 45 of absorbent core 42 and coextensively extend outwardly therefrom. Elastic strands 43 are secured intermediate topsheet 41 and backsheet 37 adjacent the longitudinal side edges 46 and 47 of insert 35. Thus, the laminated regions of the backsheet and topsheet disposed outboard of edges 44 and 45 are generally referred to as elasticized leg cuffs due to the pliability of the topsheet and the backsheet in combination with the elasticity of the elastic strands 43. However, the most effective portion of these cuffs with respect to liquid sealing is the portion disposed immediately adjacent the elastic strands. Thus, lines of tension induced sealing are principally disposed—when the insert is applied to a wearer as described hereinbefore—intermediate the outer surface of topsheet 41 and the skin of the wearer in the zones disposed between the pairs of elastic strands; one line or band of sealing for each pair of elastic strands.

FIG. 6, taken along section line 6—6, FIG. 2, shows an adhesive area 39 on a corner of the backsheet 37 of a fragmentary portion of an insert 35, FIG. 2, and a captive peelable cover 38 disposed in its factory applied position. In this position, one end of the cover 38 is permanently (i.e., non-releasably) adhered to the backsheet 37 with adhesive 48; and the other end of the cover 39 is coated with a release coating 49 which renders the cover peelable from adhesive 39, but captive with respect to the insert 35 even after being peeled from adhesive 39. As also shown in FIG. 6, the distal end of cover 38 is turned under and secured to itself to provide a grasping portion albeit it is not intended to thereby limit the present invention.

FIG. 7 is a fragmentary sectional view which, essentially, shows the structure of FIG. 6 after the cover 38 has been peeled back to uncover adhesive 39, and after adhesive 39 has been secured to a portion of the inwardly facing surface 77 of diaper 75. Thus, covers 38 of insert 35 are captive; permanently joined to insert 35 to obviate severable members which might present a trash disposal problem or, perhaps, precipitate a safety problem.

Figure 8:
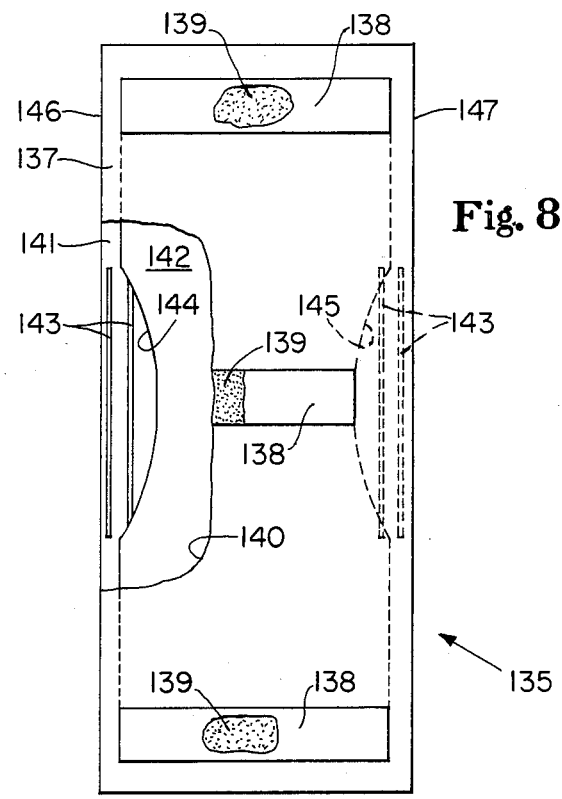
FIG. 8 is a plan view of an alternate insert embodiment looking at the outwardly facing surface of the backsheet thereof, and having portions of the backsheet torn away to reveal underlying structure.

FIG. 8 is a plan view of an alternate embodiment insert 135 which may be used to practice the present invention. The features of insert 135 which have counterpart features in insert 35 have the same designators increased by 100: e.g., insert 35 versus insert 135. Insert 135 is preferably constructed of the same materials (i.e., topsheet material, backsheet material, elastic strands, and absorbent core) as insert 35, FIG. 2. However, insert 135 exemplifies very low cost executions wherein the overall plan-view size is little more than the plan-view size of core 142; and the core is very thin and light. For example, an exemplary core having width and length dimensions of about five-and-one-half inches by about fourteen inches (about 14 by 36 cm), respectively, has been provided having a nominal-thickness of about 1.4 mm and an airfelt weight of about 14.4 grams. This embodiment has concave edges in the crotch region with a minimum width of about four inches (about 10 cm). As indicated on FIG. 8, insert 135 has three adhesive areas 139 having peelable covers 138; and its leg flaps 136 are only elasticized adjacent the crotch region although it is not intended to thereby limit the present invention. Indeed, it is believed that adhesive areas disposed in the 4 corners would be sufficient for energizing the elasticized leg cuffs as with insert 35. As with insert 35, the core is preferably in the range of from about 15 percent to about 35 percent of the waistband girth of a prospective wearer with the waistband width being somewhat greater than one-quarter the waistband girth of a wearer and the crotch width being somewhat less: e.g., five-and-one-half inches and four inches, respectively, as stated above.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A composite waste-containment garment comprising an over-garment having elasticized leg cuffs and liquid impervious construction, an insert having elasticized leg cuffs and a liquid impervious backsheet, and means integral with said insert for securing said insert inside said over-garment so that said leg cuffs of said insert are sealingly tensioned in juxtaposition with skin areas of the wearer when said over-garment having a said insert secured therewithin is applied to an intended wearer, said composite waste-containment garment further comprising an outer-garment which comprises elasticized leg cuffs and liquid impervious construction, said outer-garment further comprising side-closure means which are so disposed and configured to sealingly tension said leg cuffs of said outer-garment in addition to sealingly tensioning said leg cuffs of said insert upon applying said composite garment to a wearer and securing said side-closure means, said outer-garment being sized and configured relative to said insert and said over-garment that said composite garment can be applied to a wearer so that the leg cuffs of said insert are disposed inboard of the longitudinal side edges of said over-garment, and so that the leg cuffs of said outer-garment are disposed outboard of the longitudinal side edges of said over-garment.

2. The composite waste-containment garment of claim 1 wherein said means for securing comprises adhesive means disposed on the outwardly facing corner areas of said insert.

3. The composite waste-containment garment of claim 2 further comprising peelable cover means on said adhesive means which cover means are adapted to be peeled from said adhesive means prior to securing said insert in said over-garment.

4. The composite waste-containment garment of claim 3 further comprising means for maintaining said peelable cover means in secured relation to said insert after being peeled from said adhesive means.

5. The composite waste-containment garment of claim 1 wherein said insert further comprises an absorbent core having a nominal width of from about fifteen to about thirty-five percent of the midsection girth of said wearer.

6. The composite waste-containment garment of claim 5 wherein said core has a nominal width of about one-quarter of the midsection girth of a nominally sized wearer.

7. The composite waste-containment garment of claim 5 wherein said absorbent core of said insert has a crotch region somewhat reduced in width relative to its waist regions whereby said absorbent core has a somewhat hourglass shape.

8. The composite waste-containment garment of claim 1 wherein said over-garment is a rectangular-shape reuseable diaper comprising absorbent, launderable fabric.

9. A composite waste-containment garment comrising a generally planar, liquid pervious, liquid absorptive over-garment having no integral side-closure means and which is configured to be secured about the lower torso of a wearer with a medial portion thereof extending between the legs of the wearer, a liquid absorptive insert having elasticized leg cuffs and a liquid impervious backsheet, and means integral with said insert for securing end portions of said insert to inwardly facing surfce regions of said over-garment when said insert and said over-garment are juxtaposed and while said inner member is maintained in a non-contracted state so that said leg cuffs will become tension energized when said composite garment is formed about and secured on a wearer, said over-garment and said insert being so sized and configured relative to each other that longitudinally extending side edge regions of said over-garment can be disposed outboard of said leg cuffs when said garment is applied to and secured about a wearer.

10. A composite waste-containment garment comprising a generally planar, liquid pervious, liquid absorptive over-garment having no integral side-closure means and which is configured to be secured about the lower torso of a wearer with a medial portion thereof extending between the legs of the wearer, a liquid absorptive insert having elasticized leg cuffs and a liquid impervious backsheet, and means integral with said insert for securing end portions of said insert to inwardly facing surface regions of said over-garment when said insert and said over-garment are juxtaposed and while said inner member is maintained in a non-contracted state so that said leg cuffs will become tension energized when said composite garment is formed about and secured on a wearer, said composite garment further comprising an outer-garment having elasticized leg cuffs and a liquid impervious construction which outer-garment is adapted to be worn over said over-garment and which is so sized and configured that the elasticized leg cuffs of said outer-garment can be positioned outboard of said leg cuffs of said insert, and with the side edge regions of said over-garment disposed therebetween.

11. The composite waste-containment garment of claim 9 further comprising an outer-garment having elasticized leg cuffs and a liquid impervious construction which outer-garment is adapted to be worn over said over-garment and which is so sized and configured that the elasticized leg cuffs of said outer-garment can be positioned outboard of said leg cuffs of said insert, and with the side regions of said over-garment disposed therebetween.

* * * * *